United States Patent
Ryu et al.

(10) Patent No.: US 6,912,479 B2
(45) Date of Patent: Jun. 28, 2005

(54) HEAVY EQUIPMENT HAVING OIL POLLUTION DEGREE DIAGNOSING FUNCTION, AND OIL POLLUTION DEGREE MEASURING SYSTEM ON NETWORK USING THE SAME, AND OPERATION METHOD

(75) Inventors: Byung Jin Ryu, Kyungsangnam-do (KR); Young Jin Son, Kyungsangnam-do (KR); Ho Jin Kang, Kyungdangnam-do (KR); Dong Jun Kim, Kyungdangnam-do (KR)

(73) Assignee: Volvo Construction Equipment Holding Sweden AB, Eskilstuna (SE)

( * ) Notice: Subject to any disclaimer, the term of this patent is extended or adjusted under 35 U.S.C. 154(b) by 23 days.

(21) Appl. No.: 10/464,600

(22) Filed: Jun. 18, 2003

(65) Prior Publication Data

US 2004/0128107 A1 Jul. 1, 2004

(30) Foreign Application Priority Data

Dec. 26, 2002 (KR) ................................ 10-2002-0084222
Feb. 17, 2003 (KR) ................................ 10-2003-0009717

(51) Int. Cl.$^7$ ........................... G06F 11/30; G21C 17/00
(52) U.S. Cl. ..................................................... 702/183
(58) Field of Search ............................. 702/35, 40, 45, 702/49, 50, 81, 82, 84, 100, 182–185; 73/54.01, 54.02

(56) References Cited

U.S. PATENT DOCUMENTS 5,739,916 A    4/1998  Englehaupt 6,575,018 B2 * 6/2003 Berndorfer et al. ........ 73/54.01
2001/0013247 A1   8/2001 Wilson et al.

FOREIGN PATENT DOCUMENTS

JP         2000303504      10/2000

OTHER PUBLICATIONS

English Translation of JP 2000–303504, Atsushi, Oct. 30, 2000.*

Derwent English Abstract of JP 2000303504 Dated Oct. 31, 2000.

* cited by examiner

*Primary Examiner*—Michael Nghiem
(74) *Attorney, Agent, or Firm*—Ladas & Parry LLP (57) ABSTRACT

The present invention relates to a heavy equipment having an oil pollution degree diagnosing function, and an oil pollution degree measuring system on a network using the same, and an operation method, and in particular to a heavy equipment which is capable of measuring a pollution state of an engaging chain heavy equipment oil of a complicated hydraulic apparatus based on a phenomenon that an intensity of a transmitting light is different based on the amount of a pollution particle contained in an oil by transmitting a sensor light into an oil which circulates in a heavy equipment which is driven by a hydraulic system, and an oil pollution degree measuring system on a network, and an operation method of the same which are capable of diagnosing an oil measuring value of each heavy equipment in a remote server and informing an oil exchanging time and an abnormal state of a hydraulic system.

6 Claims, 8 Drawing Sheets

| Type of analysis | Section I | Section II | Section III |
|---|---|---|---|
| NaS1638 analysis class | 7-8 | 8-9 | 10-11 |
| ICP analysis(Fe) PPM | 3.0-7.6 | 9.2-28.5 | 26.5-48.1 |
| ICP analysis(Cu) PPM | 12.8-19.5 | 34.2-66.3 | 52.1-113.0 |
| ICP analysis(Zn) PPM | 426-437 | 396-417 | 343-426 |
| Spectroscopy analysis (Fe) PPM | 2.4-5.8 | 7.6-41.6 | 65.7-97.0 |
| Spectroscopy analysis (Cu) PPM | 10.2-16.5 | 27.1-53.0 | 92.5-154.5 |
| Spectroscopy analysis (Zn) PPM | 445-455 | 394-405 | 318-412 |
| Kinematic viscosity (40°C)D445 | 42.14-44.56 | 43.32-44.07 | 42.34-43-23 |
| Kinematic viscosity (100°C)D445 | 7.52-7.94 | 7.37-7.42 | 7.33-7.6 |
| Outer shape visual | Bright | Bright | Bright |
| Viscosity index | 140-147 | 135-136 | 139-141 |
| Total acid number D664 | 0.56-0.63 | 0.41-0.68 | 0.45-0.55 |
| Moisture, Vol% | Negative | Negative | Negative |
| Operation oil state | Normal | Normal (particle growing, filter exchange) | Abnormal (oil exchange) |
| Online monitoring alarming step | GREEN(G1-G3) | GREEN-BULE(G3-Y1) | BULE-RED(Y2-R1) |

FIG.9

HEAVY EQUIPMENT HAVING OIL POLLUTION DEGREE DIAGNOSING FUNCTION, AND OIL POLLUTION DEGREE MEASURING SYSTEM ON NETWORK USING THE SAME, AND OPERATION METHOD

BACKGROUND OF THE INVENTION

1. Field of the Invention

The present invention relates to a heavy equipment having an oil pollution degree diagnosing function, and an oil pollution degree measuring system on a network using the same, and an operation method, and in particular to a heavy equipment which is capable of measuring a pollution state of an engaging chain heavy equipment oil of a complicated hydraulic apparatus based on a phenomenon that an intensity of a transmitting light is different based on the amount of a pollution particle contained in an oil by transmitting a sensor light into an oil which circulates in a heavy equipment which is driven by a hydraulic system, and an oil pollution degree measuring system on a network, and an operation method of the same which are capable of diagnosing an oil measuring value of each heavy equipment in a remote server and informing an oil exchanging time and an abnormal state of a hydraulic system.

2. Description of the Background Art

Generally, a heavy equipment is used for excavating soils or rocks in a construction site. As one of representative driving control methods, a hydraulic method is generally used. Since the above heavy equipment is driven in a high load and long time operation state, a durability of a heavy equipment and an easier maintenance are important comparison references for judging a performance of a heavy equipment.

A hydraulic oil which flows in the interior of a hydraulic system which performs a major operation of a heavy equipment may lose a lubricating function due to an oxidation, degradation, consumption of additives, etc. by a bad condition of use of elements of a hydraulic circuit line such as a hydraulic pump, hydraulic motor (track, circulation), MCV (main control valve), RCV (remote control valve), pipe, hose, hydraulic tank, oil cooler, etc. At this time, when an exchange of a hydraulic oil filter and oil is properly performed, a normal state of a heavy equipment component is maintained, and an efficiency of an equipment is enhanced. In addition, a durability of an equipment is enhanced in a construction site, so that a life span of an equipment is extended.

As a state diagnosing method of a heavy equipment hydraulic system, a fixed quantity/qualitative analysis of a sampled oil which is obtained based on a direct extraction of an oil from an equipment is preferred as a state diagnosing method of an accurate oil for judging a state of a hydraulic state. Generally, a state diagnosis of an oil is used for a diagnosis of various diseases through a sample analysis through a blood extraction of human. It is possible to understand a state of an equipment element through a fixed quantity of a small amount of an additive and metal particle based on a fixed quantity computation and ICP analysis of a metal particle through a physical characteristic test of a kinematic viscosity, viscosity index, oxidation stability, rust preventive property, foam formation prevention characteristic, etc. of a sampled oil, a fixed quality analysis of a particle size based on an analysis by a particle counter, and a qualitative analysis by a ferrography analysis and a SEM/EDM analysis.

In the work of an oil pollution degree evaluation performed in a conventional offline, a sampling is performed in a work site. In addition, the cost and period are increased because there are a number of sampling oil works, an over period and cost due to a sampling oil analysis in an analyzing organ, and a certain procedure such as a feed back in an after sale center.

In addition, in the conventional sampling work, a human initiated extraction work is performed by an expert worker, so that a dependency with respect to a worker is increased. A failure may occur due to an error of a worker. The work for managing an oil pollution state and history of each heavy equipment needs a man power and is a time consuming work.

Furthermore, a check of a heavy equipment based on an oil pollution diagnosis is directed to enhancing a durability of a heavy equipment and extending a life span of the same. In the case that a proper measurement is not provided, a work efficiency of a heavy equipment is decreased, and a certain danger accident may occur due to a malfunction during an operation.

Therefore, an oil pollution degree measuring system on a network and an operating method of the same are needed, which are capable of managing an oil pollution degree in a central server with respect to a heavy equipment which is directed to performing a checking function of a filter exchanging time, an oil flushing time, an exchanging time, an abnormal state detection in real time and a heavy equipment in a construction site in such a manner that in a work environment for evaluating an oil pollution in a conventional art, an oil sate is diagnosed based on an efficient, simple and direct method, and an oil pollution state and its history with respect to each heavy equipment are managed in a central server.

SUMMARY OF THE INVENTION

Accordingly, it is an object of the present invention to provide an oil pollution degree measuring system for a heavy equipment on a network, and an operation method of the same which are capable of providing a sensor unit adapted to detect a state of an oil in a hydraulic system of a heavy equipment, diagnosing an oil state based on an exchanging time of a filter, an oil flushing time, an exchanging time, and a detection of an abnormal state of oil by receiving a sensor value remotely, displaying on a display unit of a heavy equipment and informing to an operator.

To achieve the above objects, in a heavy equipment having a hydraulic circuit line which is formed of a hydraulic pump, a hydraulic motor, a major adjusting valve, a remote adjusting valve, a pipe, a hose, a hydraulic tank and an oil cooler, there is provided a heavy equipment having an oil pollution degree diagnosis function which comprising a sensor unit which is installed in such a manner that an oil is flown into the interior of the same in a hydraulic circuit of the heavy equipment and is adapted to extract an oil flowing in the hydraulic circuit and to measure an oil pollution state sensor value; a control unit which is adapted to diagnose a normal/abnormal state of a heavy equipment hydraulic system, filter check/exchange, oil exchange, emergency stop, etc. by an oil pollution state diagnosis program formed of a certain algorithm with respect to the sensor value detected through the sensor unit; a communication unit which receives a sensor value and a result value from the sensor unit and the control unit, respectively and transfers to the outside and receives a return value of a result of process from the outside; a storing unit which stores a sensor value of the sensor unit, a result value of the control unit, a return value of the communication unit, and other related data; and a display unit which informs an oil pollution state to an operator based on the sensor value, result value and return value; whereby an oil pollution degree of a heavy equipment is measured by controlling the sensor unit, communication unit, storing unit and display unit by the control unit and is informed to the operator.

The sensor unit includes a sensor block which forms an outer construction of the same; an oil extracting apparatus which is installed in the oil circuit in such a manner that an oil is flown thereinto, for thereby extracting an oil; a light emitting apparatus which is provided in a rear end of the oil extracting apparatus and generates a sensor light which transmits the extracted oil; a reflection mirror which is installed in a front end of the oil extracting apparatus and reflects a sensor light which transmitted the extracted oil; a light receiving apparatus which is provided in a rear end of the oil extracting apparatus and measures an intensity of the reflection light which transmitted the extracted oil by the reflection mirror; and an optical sensor unit which inputs the light from the light emitting apparatus into the extracted oil as a parallel light and includes an optical transfer apparatus which transfers the reflection light which was reflected by the reflection mirror and transmitted the monitored oil to the light receiving apparatus.

In order to achieve the above objects, there is provided an oil pollution degree measuring system of a heavy equipment on a network as a system for remotely measuring and diagnosing an oil pollution degree between a heavy equipment and an oil pollution diagnosis server on a network, comprising a hydraulic heavy equipment which includes a sensor unit which is installed in a hydraulic circuit of the heavy equipment in such a manner that an oil is flown into the interior of the same and extracts an oil flowing in the hydraulic circuit and measures an oil pollution state sensor value; a control unit which is adapted to diagnose a normal/abnormal state of a heavy equipment hydraulic system, filter check/exchange, oil exchange, emergency stop, etc. by an oil pollution state diagnosis program formed of a certain algorithm with respect to the sensor value detected through the sensor unit; a communication unit which receives a sensor value and a result value from the sensor unit and the control unit, respectively and transfers to the outside and receives a return value of a result of process from the outside; a storing unit which stores a sensor value of the sensor unit, a result value of the control unit, a return value of the communication unit, and other related data; and a display unit which informs an oil pollution state to an operator based on the sensor value, result value and return value; and an oil pollution diagnosis server which includes a server communication unit which receives an inherent heavy equipment ID, the sensor value and a receiving data including a result value from the communication units of a plurality of heavy equipments and transmits a return value corresponding to a result of a process to the communication unit of the heavy equipment corresponding to the heavy equipment ID; a storing unit which stores an engine driving time, measuring number, the sensor value and a receiving data including the result value based on the heavy equipment ID received from the server communication unit; and a server control unit which controls the server communication unit and the storing unit for processing the receiving data, whereby the heavy equipment measures an oil pollution state in a sensor value and determines a result value and transmits to the oil pollution diagnosis server, and the oil pollution diagnosis server receives a data from a plurality of the heavy equipments and stores the same and transmits a result return value to a corresponding heavy equipment.

To achieve the above objects of the present invention, according to a first embodiment of the present invention, there is provided an oil pollution degree measuring method of a heavy equipment on a network as a method for remotely measuring and diagnosing an oil pollution degree between a heavy equipment and an oil pollution diagnosis server on a network, comprising the steps of a step (1) in which an oil pollution state sensor value is measured by transmitting a sensor light in a sensor unit of a hydraulic circuit provide in a certain portion of a heavy equipment; a step (2) in which a sensor value determines an oil pollution state result value by judging a normal/abnormal state of a heavy equipment hydraulic system, a filter check/exchange, oil exchange, emergency stop, etc. by an oil pollution state diagnosis program in a control unit of the heavy equipment; a step (3) in which a server communication unit of an oil pollution diagnosis server receives a sensor value and a result value from a communication unit of the heavy equipment; a step (4) in which an engine driving time, a measuring number, and a data of the sensor value and result value based on a heavy equipment ID are stored in the storing unit in accordance with a control of the server control unit of the oil pollution diagnosis server; a step (5) in which the server communication unit transfers a result of a process processed by the server control unit to a communication unit of the heavy equipment as a return value; a step (6) in which a control unit of the heavy equipment displays an oil pollution state on a display unit based on the sensor value, result value and return value, whereby the heavy equipment measures an oil pollution state as a sensor value and determines a result value and transmits to the oil pollution diagnosis server, and the oil pollution diagnosis server receives a data from a plurality of heavy equipments and stores the same and transfers a result return value to an individual heavy equipment.

To achieve the above objects, there is provided an oil pollution degree measuring system of a heavy equipment on a network as a system for remotely measuring and diagnosing an oil pollution degree between a heavy equipment and an oil pollution server on a network, comprising a hydraulic heavy equipment which includes a sensor unit which is installed in such a manner that an oil is flown into the interior of the same in a hydraulic circuit of the heavy equipment and is adapted to extract an oil flowing in the hydraulic circuit and to measure an oil pollution state sensor value; a communication unit which transfers a sensor value of the sensor unit to the server and receives a process result value concerning an oil pollution state from the server; a storing unit for storing a sensor value of the sensor unit, a result value of the communication unit and other related data; a display unit for informing an oil pollution state to an operator based on the sensor value and result value; and a control unit for controlling the sensor unit, communication unit, storing unit and display unit; and an oil pollution diagnosing server which includes a server communication unit which receives an inherent heavy equipment ID and a receiving data including the sensor data from a communication unit of a plurality of heavy equipments and transfers a result value corresponding to a process result to the communication unit of the heavy equipment corresponding to the heavy equipment ID; a server control unit which diagnoses a normal/abnormal state, filter check/exchange, oil exchange, emergency stop, etc. of a hydraulic system of a heavy equipment by an oil pollution state diagnosis program formed of a certain algorithm with respect to a sensor value that the server communication received and determines an oil pollution state result value and transfers the result value to the server communication unit; and a storing unit which stores an engine driving time, measuring number, a receiving data including the sensor value and a result value data of the server control unit based on the heavy equipment ID received through the server communication unit, whereby the heavy equipment measures an oil pollution state as a sensor value and transfers to the oil pollution diagnosis server, and the oil pollution diagnosis server receives a data from a plurality of the heavy equipments and determines an oil pollution state result value and transfers the result value to a corresponding heavy equipment.

To achieve the above objects, according to a second embodiment of the present invention, there is provided an oil pollution degree measuring method of a heavy equipment on a network as a method for remotely measuring and diagnosing an oil pollution degree between a heavy equipment and an oil pollution diagnosis server on a network, comprising the steps of a step (1) in which an oil pollution state sensor value is measured by transmitting a sensor light in a sensor unit of a hydraulic circuit provide in a certain portion of a heavy equipment; a step (2) in which a server communication unit of the oil pollution diagnosis server receives a sensor value from a communication unit of the heavy equipment; a step (3) in which the sensor value is adapted to judge a normal/abnormal state of a heavy equipment hydraulic system, a filter check/exchange, an oil exchange, an emergency stop, etc. by a certain oil pollution stare diagnosis program in the server control unit of the oil pollution diagnosis server, for thereby determining an oil pollution state result value; a step (4) in which an engine driving time, measuring number, sensor value and result value data based on the heavy equipment ID are stored in the storing unit based on a control of the server control unit of the oil pollution diagnosis server; a step (5) in which the server communication unit transfers a result processed by the server control unit to the communication unit of the heavy equipment as a result value; and a step (6) in which the control unit of the heavy equipment displays an oil pollution state on the display unit based on the sensor value and the result value, whereby the heavy equipment measures an oil pollution state as a sensor value and transfers to the oil pollution diagnosis server, and the oil pollution diagnosis server receives a data from a plurality of the heavy equipments and determines an oil pollution state result value and transfers the result value to a corresponding heavy equipment.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION OF THE PREFERRED EMBODIMENTS

The technical construction of the present invention is classified into a first construction of a heavy equipment having an oil pollution degree diagnosing function, a second construction of an oil pollution degree measuring system on a network using the above heavy equipment, and a third construction of an operation method of an oil pollution degree measuring system. In addition, the second and third constructions are referred to a first embodiment of the present invention for measuring and diagnosing an oil pollution degree in a heavy equipment, and a second embodiment of the present invention for measuring and diagnosing an oil pollution degree in an oil pollution diagnosing server according to the present invention.

The preferred embodiments of the present invention will be described in detail with reference to the accompanying drawings.

Figure 1:
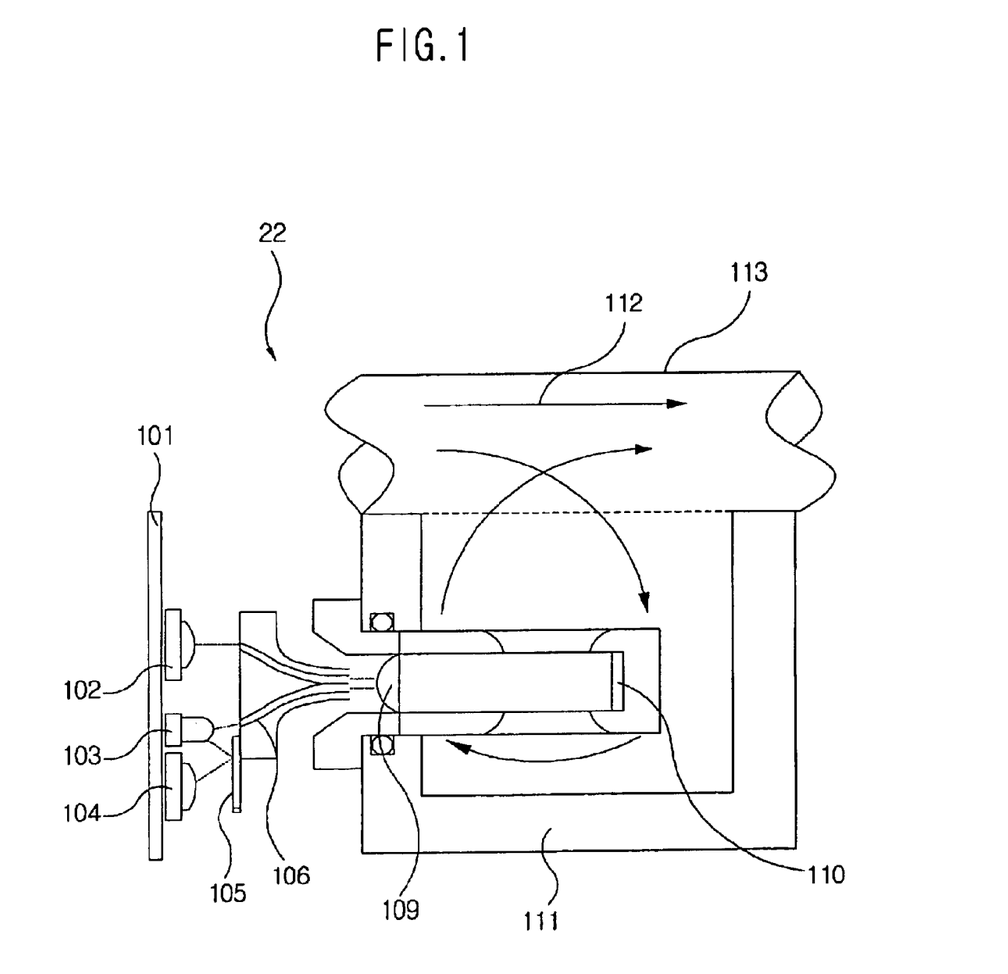
FIG. 1 is a view illustrating the construction of a sensor unit installed in a heavy equipment according to the present invention.

FIG. 1 is a view illustrating the construction of a sensor unit installed in a heavy equipment for implementing an oil pollution degree diagnosing function according to a first construction of the embodiment of the present invention.

In the heavy equipment of the present invention, the sensor unit 22 includes a sensor block 111 which forms an outer construction of the same, an apparatus for extracting an oil 112 by a certain amount which flows in an oil pipe 113 through a certain machine apparatus, a light emitting apparatus which generates an incident light which transmits the extracted oil, a reflection mirror which reflects a light which transmitted the extracted oil, a light receiving apparatus for measuring the intensity of a light which is reflected by the reflection mirror and transmitted the extracted oil, and a sensor unit 22 which is capable of inputting a light from the light emitting apparatus into the extracted oil as a parallel light through a lens and transferring the reflection light which was reflected by the reflection mirror and transmitted the extracted oil to the light receiving apparatus.

In the real time oil pollution degree measuring sensor unit 22 according to the present invention, an infrared ray light emitting diode 103 which forms the light emitting apparatus and a light receiving photo diode 104 which forms a light receiving apparatus are installed on the same vertical straight line for optimizing the sizes, and the light from the infrared ray light emitting diode 103 of the light emitting apparatus is reflected through a reflection plate by installing the reflection plate 105 and is received by the light receiving photodiode 104 of the light receiving apparatus.

The sensor unit 22 according to the present invention includes one optical lens 109 based on the construction that the light from the infrared ray light emitting diode 103 is received and reverse-reflected by the reflection mirror 110 to the photo diode 102 of the light receiving apparatus through an optical transfer apparatus 106.

A controller 21 includes an oil pollution state diagnosing program and preferably includes a storing unit 25 which is capable of receiving a data concerning an oil pollution degree measured from the sensor unit 22 and storing a data of an oil pollution degree based on an engine hour meter.

The signals based on the steps such as a normal, filter checking/exchange, oil exchange, emergency stop, etc. which are determined in connection with a corresponding oil state based on an algorithm of an oil pollution state diagnosing program of the controller 21 is reported to a display unit 24 with respect to the data from the sensor unit 22.

The data stored in the storing unit 25 of the heavy equipment 2 are accumulated by the data such as a value of an oil pollution degree based on a corresponding engine driving time and a data of a display unit of a corresponding oil step and are downloadable from the server 3 at the next time. The data may represent a history with respect to the oil state of the equipment.

The display unit 24 is installed in a cap which is a use space of a driver and displays an oil pollution data of a heavy equipment which occurs in real time from the controller 21 or a communication unit 23, so that an alarm concerning a state of an oil pollution and an emergency stop are informed to an operator by a light, LED, voice, etc.

Figure 2:
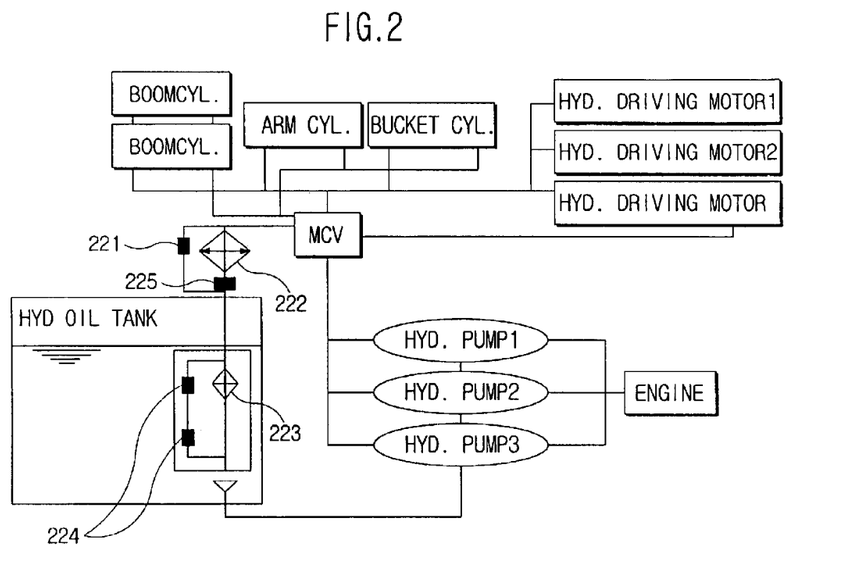
FIG. 2 is a view illustrating the construction of a hydraulic circuit of a heavy equipment having a sensor unit according to the present invention.

FIG. 2 is a view illustrating the construction of a hydraulic circuit having a sensor unit 22 of FIG. 1 installed in the heavy equipment 2. Reference numerals 221 through 225 represent positions for a sensor unit 22 based on the positions of the installation.

The sensor unit position 221 is in a bypass of an oil cooler 222 in a process that an oil is flown into an oil tank through a hydraulic pump, MCV and hydraulic actuator in a hydraulic tank in the hydraulic circuit system of the heavy equipment. In addition, the position of the sensor unit may be in an input line 225 of the oil cooler 222, or in an input or output side of a return filter 223, of its bypass line 224.

Figure 3:
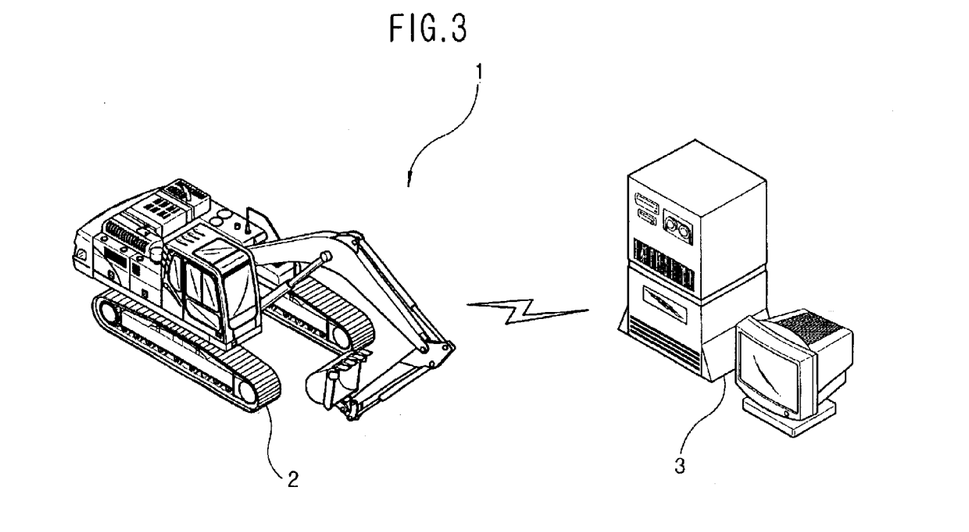
FIG. 3 is a view illustrating the construction of an execution environment of an oil pollution degree measuring system of a heavy equipment on a network according to the present invention.

FIG. 3 is a view illustrating the second construction of the present invention and illustrating an execution environment of an oil pollution degree measuring system 1 in which the heavy equipment 2 and the oil pollution diagnosing server 3 are constructed on the network in a wireless communication method. In the present invention, the sensor value which represents an impurity degree is measured through the sensor unit 22 which outputs a light with respect to the hydraulic oil which circulates in the interior of the hydraulic system of the heavy equipment 2. Next, the oil pollution degree is judged by an oil pollution state diagnosing program which is formed of a certain algorithm using the sensor value as an input value.

In the first embodiment of the present invention, a diagnosing program is provided in the controller 21 of a heavy equipment corresponding to the client based on an oil pollution state diagnosing program which is used for judging the oil pollution, and the second embodiment of the present invention provides a construction that the diagnosing program is provided in the controller 31 of the oil pollution diagnosing server corresponding to a server side.

Figure 4:
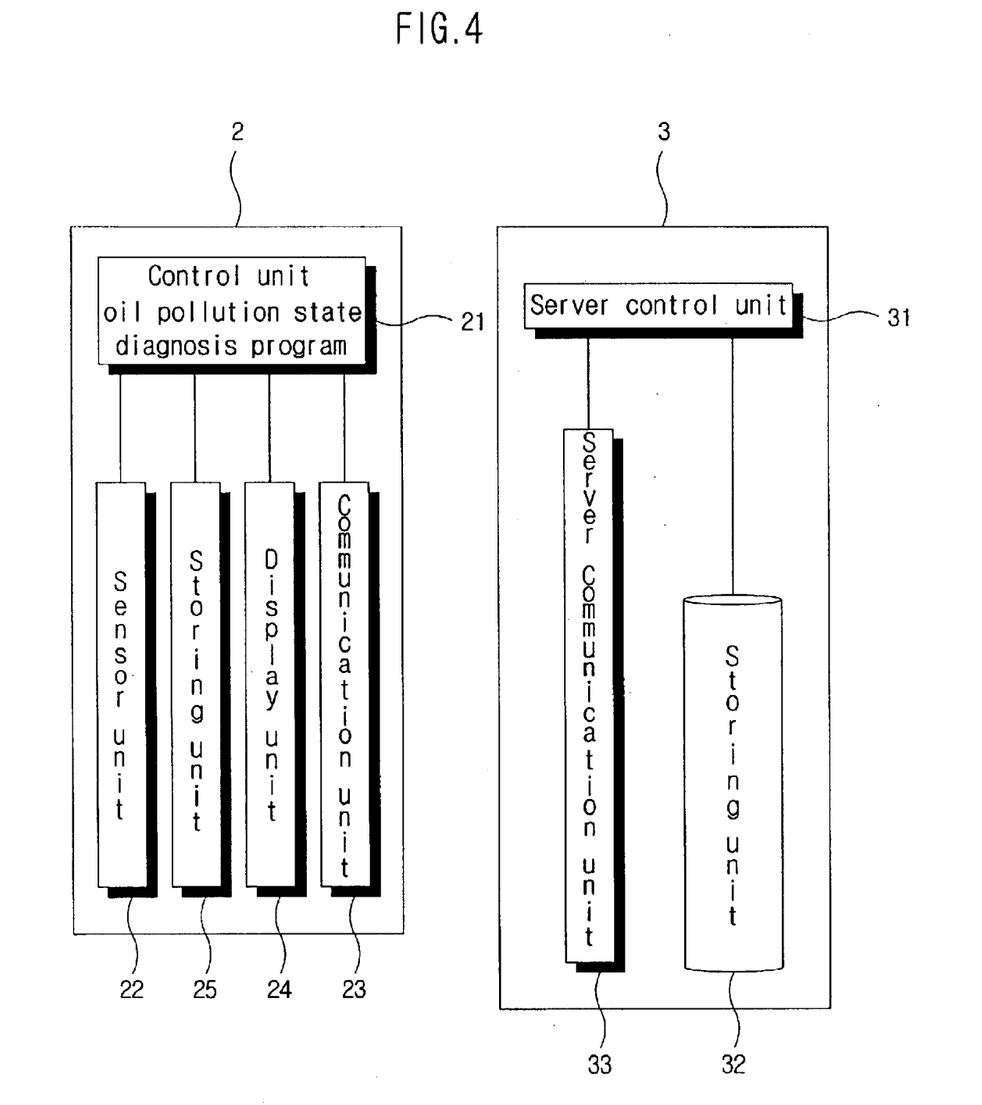
FIG. 4 is a view illustrating the construction of an oil pollution degree measuring system which is capable of diagnosing an oil pollution degree in a heavy equipment according to a first embodiment of the present invention.

FIG. 4 is a view illustrating the construction of an oil pollution degree measuring system 1 which is capable of diagnosing an oil pollution degree in the heavy equipment according to the first embodiment of the present invention. The controller 21 of the heavy equipment of the first embodiment of the present invention controls the sensor unit 22, the storing unit 25, the display unit 24, and the communication unit 23 of the heavy equipment and judges a normal and abnormal state, filter checking and exchange, oil exchange, emergency stop, etc. of the hydraulic system of the heavy equipment using an oil pollution state diagnosing program formed of a certain algorithm which is used to judge a pollution degree with respect to the sensor value measured by the sensor unit 22.

The pollution degree that the heavy equipment 2 judged as a client is transferred to the server 3, and the oil pollution diagnosing server 3 stores a result value from a plurality of heavy equipments in the storing unit 32 based on an inherent ID of each heavy equipment and integrally manages the same for thereby implementing an integral management. The server 3 integrally manages the oil pollution with respect to a plurality of the heavy equipments 2 driven in the work site for thereby implementing a best performance of the heavy equipment and enhancing a work efficiency.

Figure 5:
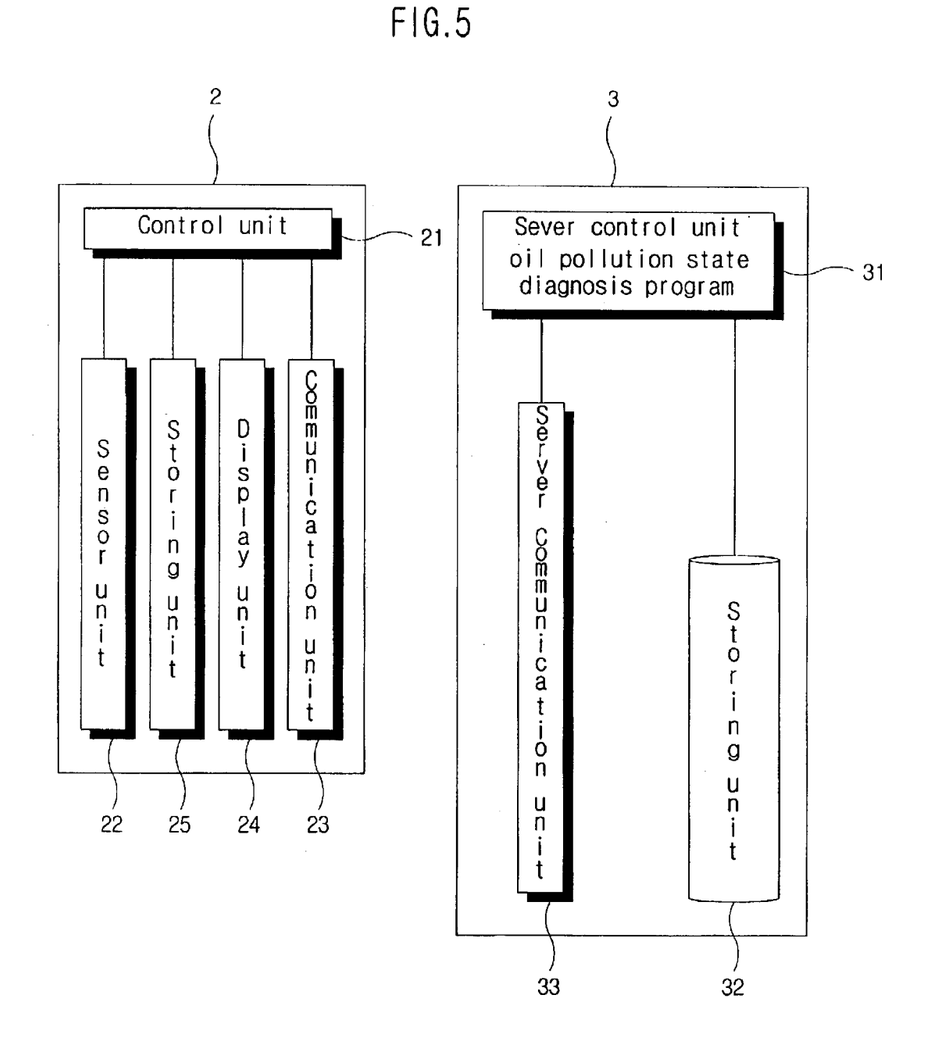
FIG. 5 is a view illustrating the construction of an oil pollution degree measuring system which is capable of diagnosing an oil pollution degree in an oil pollution diagnosing server according to a second embodiment of the present invention.

FIG. 5 is a view illustrating the construction of an oil pollution degree measuring system which is capable of measuring an oil pollution degree in the oil pollution diagnosing server 3 according to a second embodiment of the present invention. The server control unit 31 of the server side according to the second embodiment of the present invention controls the server communication unit 33 and the storing unit 32 and judges a normal/abnormal state, filter check and exchange, oil exchange, emergency stop, etc. of the hydraulic system of the heavy equipment using an oil pollution state diagnosing program formed of a certain algorithm which is capable of judging a pollution degree with respect to the sensor value received from each heavy equipment and transmitting a result of the judgment to the heavy equipment 2.

The sensor value measured by the sensor unit of the heavy equipment 2 is transmitted to the oil pollution diagnosing server 3, and the server control unit 31 judges an oil pollution degree based on an oil pollution state diagnosing program, and a result of the judgment is stored in the storing unit 32 based on an inherent ID of each heavy equipment for thereby implementing an integral management.

In the first embodiment of the present invention, a diagnosing program is individually performed in the control unit of each heavy equipment 2 with respect to a diagnosis of the oil pollution state. In the second embodiment of the present invention, since the server 3 receives a sensor value from the heavy equipments 2, and a single server control unit 31 integrally performs a diagnosis, it is advantages in economically decreasing the load of the control unit 21 of the heavy equipment.

Therefore, the first embodiment and second embodiment of the present invention may be selectively adapted based on the size of the work site. The first embodiment of the present invention is preferably adapted for a small size work site in which a small number of heavy equipments is inputted, and the second embodiment of the present invention may be preferably adapted in a large scale work site such as a plant, road construction, harbor, air port, etc. A selection switch may be adapted between the first and second embodiments of the present invention in the display unit of the heavy equipment, so that the diagnosis program is selectively executed based on the work site.

Figure 6:
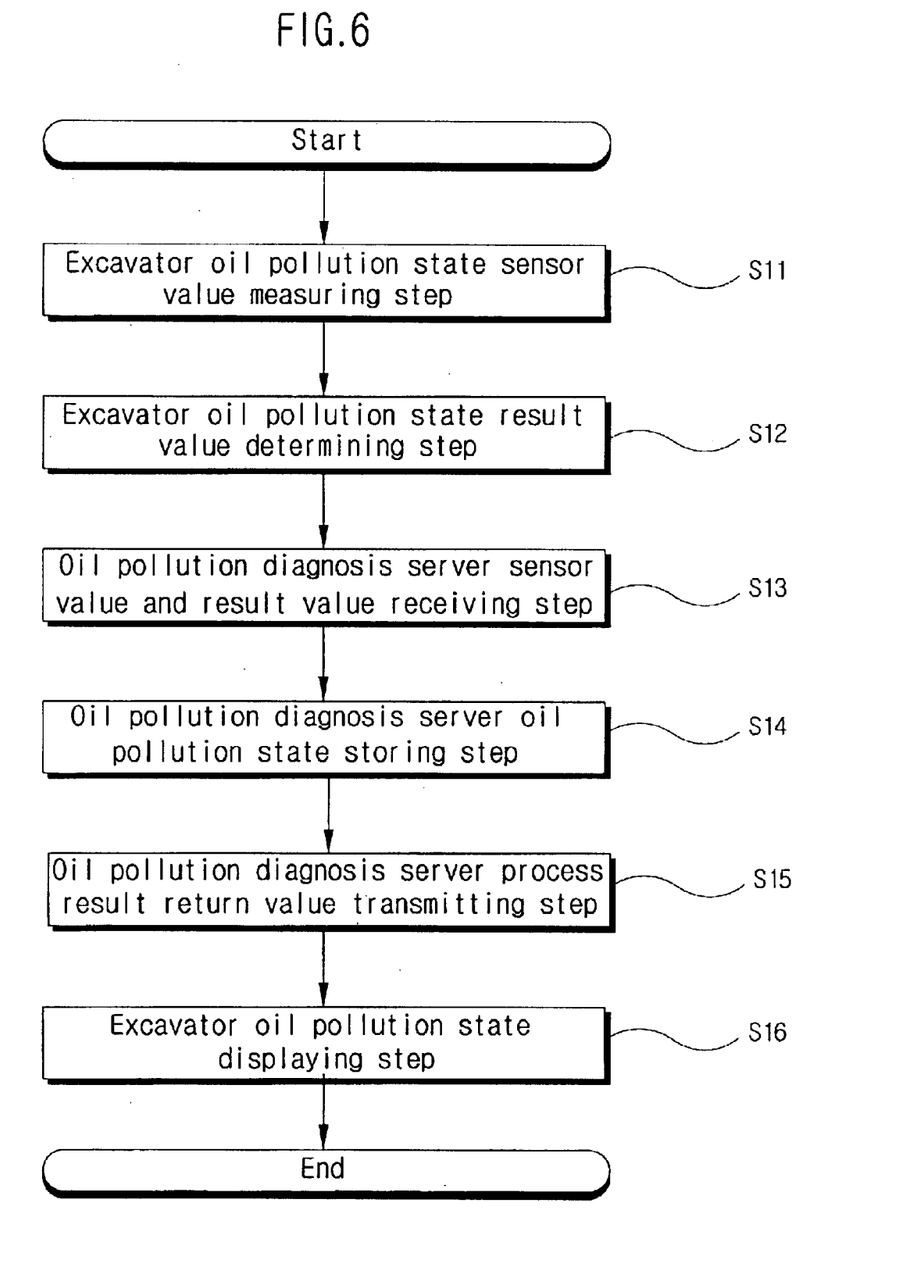
FIG. 6 is a flow chart of a process between a heavy equipment and an oil pollution diagnosing server according to a first embodiment of the present invention.
Figure 7:
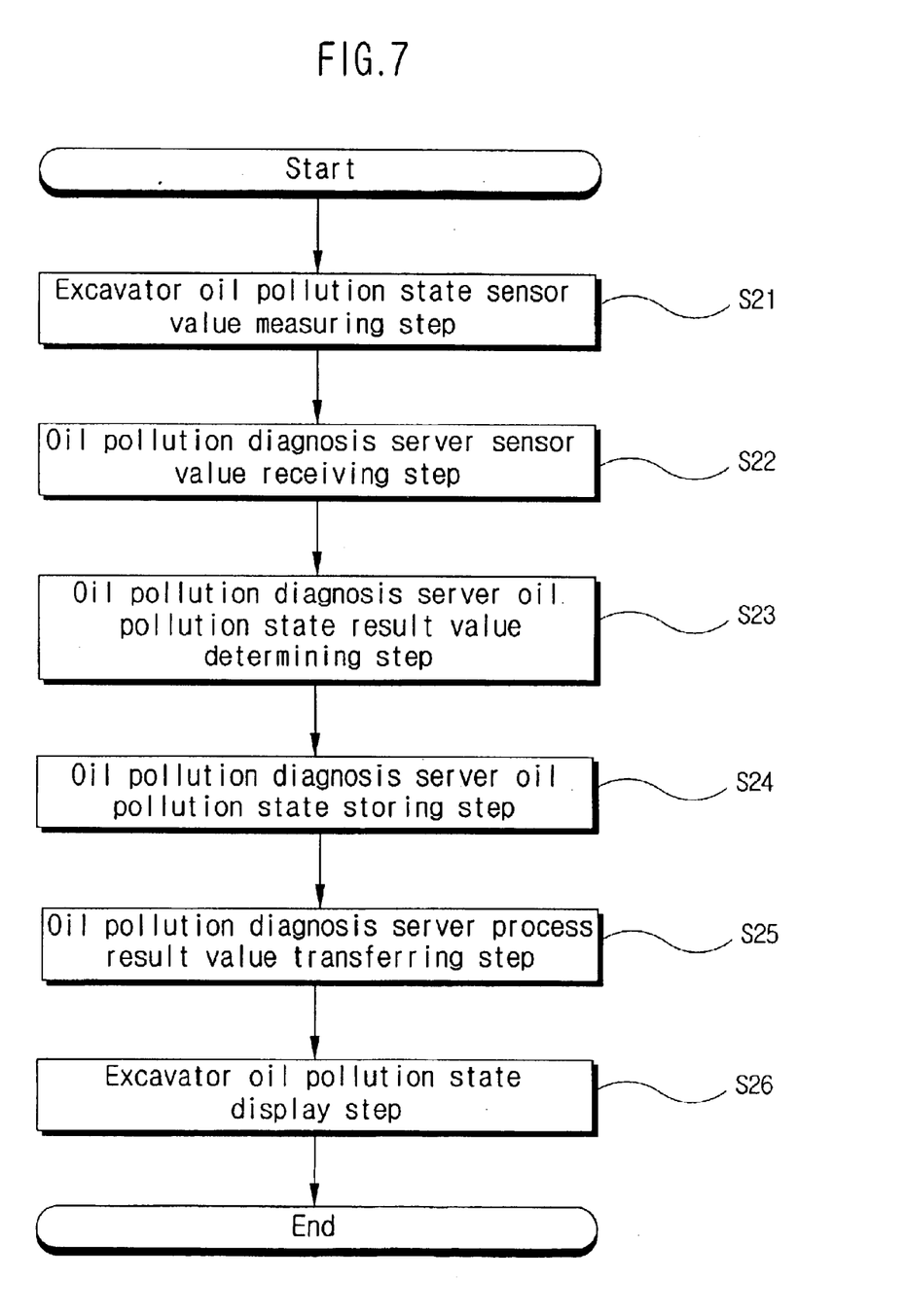
FIG. 7 is a flow chart of a process between a heavy equipment and an oil pollution diagnosing server according to a second embodiment of the present invention.

FIGS. 6 and 7 are flow charts of an oil pollution degree measuring and diagnosing method which is implemented in the oil pollution degree measuring system which is a third construction of the present invention.

FIG. 6 is a flow chart of a process between the heavy equipment and the oil pollution diagnosis server of FIG. 4. In a heavy equipment oil pollution state sensor value measuring step S11, the sensor unit 22 of the heavy equipment measures a sensor value based on an impurity material in such a manner that a light is scanned to the oil which flows in the interior at every regular time at the time when the heavy equipment is started. In a heavy equipment oil pollution state result value determining step S12, the control unit 21 of the heavy equipment diagnoses an oil pollution degree with respect to the sensor value and generates a result value.

In an oil pollution diagnosis server sensor value and result value receiving step S13, the communication unit 33 of the oil pollution diagnosis server receives a receiving data which includes a heavy equipment ID, sensor value and result value from the communication unit 23 of the heavy equipment.

In an oil pollution diagnosis server oil pollution state storing step S14, the receiving data from the heavy equipment is stored in the storing unit 32 based on a heavy equipment ID in accordance with a control of the server control unit 31. Next, in an oil pollution diagnosis server processing result return value transmission step S15, a result of the process in the side of the server and a return value corresponding to a message informed to the heavy equipment are transmitted.

In a heavy equipment oil pollution state display step S16, the communication unit 23 receives a data from the service communication unit 33 and displays on the display unit 24 of the heavy equipment based on a sensor value and result value.

FIG. 7 is a flow chart of a process between the heavy equipment and the oil pollution diagnosis server of FIG. 5 according to the second embodiment of the present invention. In a heavy equipment oil pollution state sensor value measuring step S21, the sensor unit 22 of the heavy equipment measures a sensor value based on an impurity material in such a manner that a light is scanned into an oil which flows in the interior at a certain time interval at the time when the heavy equipment is started. Next, the measured sensor value is directly transmitted to the server compared to the first embodiment of the present invention, so that the result value is computed in the oil pollution diagnosis server 3.

In an oil pollution diagnosis server sensor value receiving step S22, the communication unit 33 of the oil pollution diagnosis server receives a receiving data which includes a heavy equipment ID and sensor value from the communication unit 23 of the heavy equipment. Next, in an oil pollution diagnosis server oil pollution state result value determining step S23, the server controller 31 computes an oil pollution degree result value with respect to the sensor value received based on the diagnosis program.

In an oil pollution diagnosis server oil pollution storing step S24, the receiving data from the heavy equipment and the determination value diagnosed by the server control unit 31 are stored in the storing unit 32 based on a heavy equipment ID in accordance with a control of the server control unit 31. Next, in an oil pollution diagnosis server process result value transmitting step S25, a process result of the server side and a return value with respect to a message to be informed to the heavy equipment are transmitted.

In a heavy equipment oil pollution state display step S26, the communication unit 23 displays on the display unit 24 of the heavy equipment based on the result value data from the server communication unit 33 and a previously obtained sensor value, so that the operator is informed of an oil pollution state.

In the case of the second embodiment of the present invention, the communication traffic amount is increased between the heavy equipment and the server but it is not needed to compute the result value based on a diagnosis installation program for each heavy equipment like in the first embodiment of the present invention, so that the diagnosis is more economically performed in the oil pollution diagnosis server.

Figure 8:
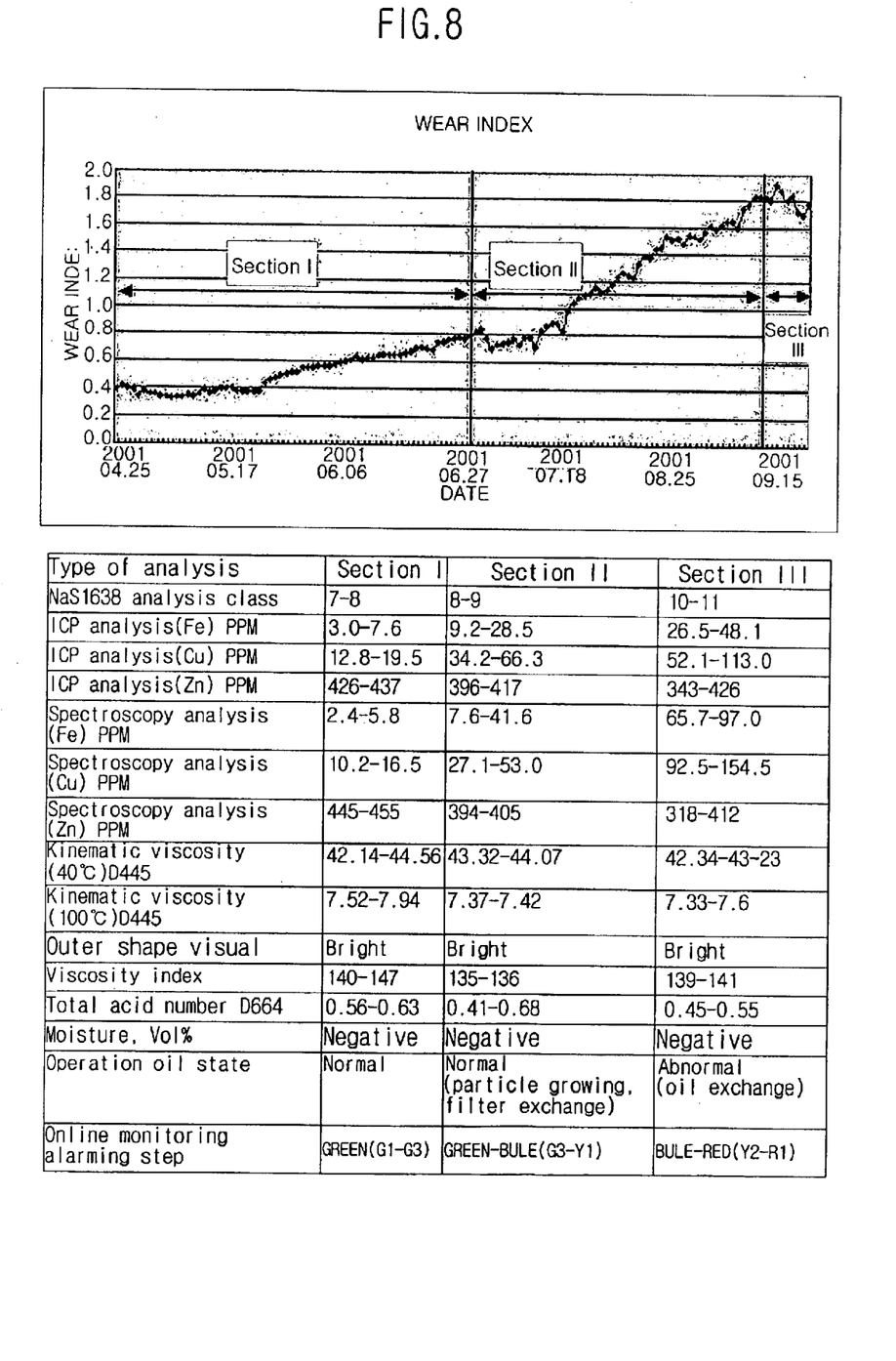
FIGS. 8 and 9 are views in which a result value of an oil pollution degree diagnosis is shown in a text and a graphic form according to the present invention.
Figure 9:
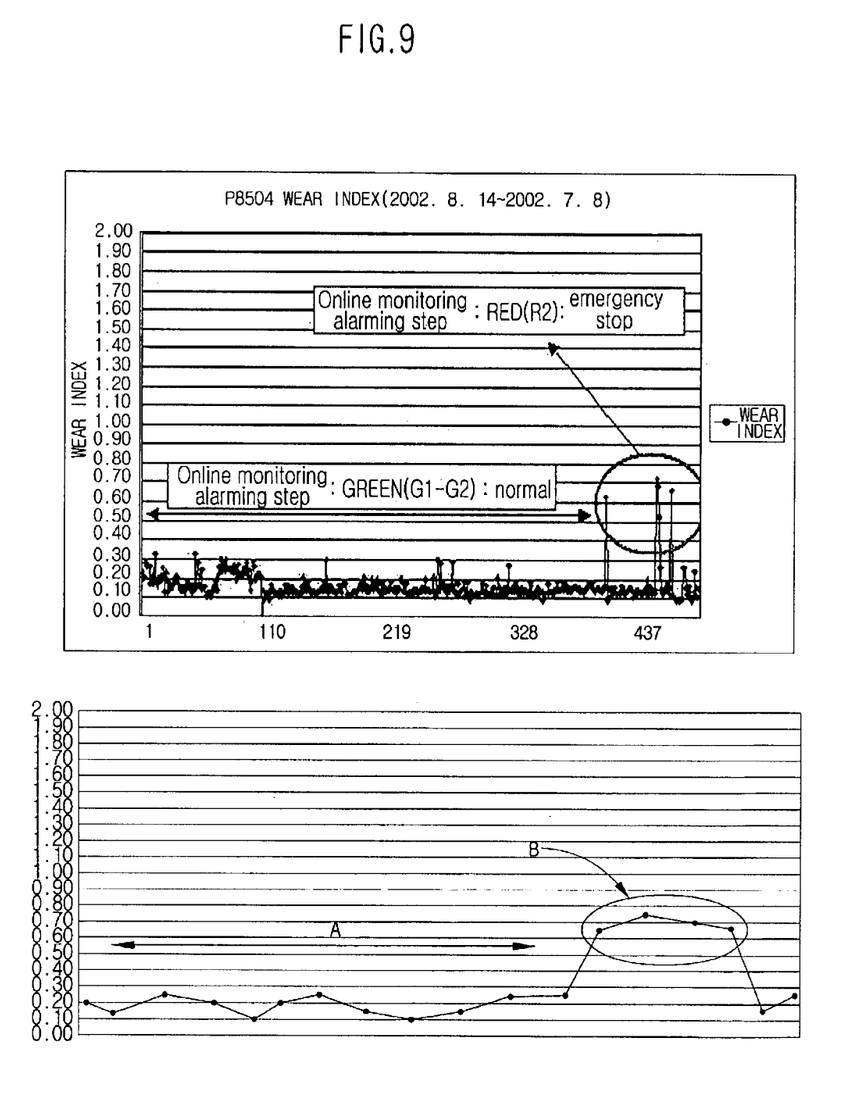

FIGS. 8 and 9 are views illustrating the oil pollution degree result values diagnosed based on the embodiment of the present invention which are expressed in the text data form and graph data form.

The oil pollution state diagnosing program which is loaded and executed by the control unit receives the sensor value measured by the sensor unit as an input value and diagnoses an oil pollution state and outputs a result of the same. The result values are outputted based on the steps such as the grades G1, G2, G3 and G4 determined based on the pollution degree, filter check/exchange (Y1, Y2), oil exchange, emergency stop R2, etc. in accordance with a process of the diagnosis algorithm, and the display unit receives the above values and expresses in the text or graph forms.

In FIG. 8, the upper drawing illustrates a wear (pollution) index in the sections I, II and III, and the lower drawing illustrates a result of the same in a table form. In addition, the lower drawing illustrates a result item (entire portion except for the lower most items of the analysis kinds) that the worker directly extracted through the samplings in the offline, and the result (network monitoring alarm step in the lower most item in the vertical axis) experimented based on the construction of the embodiments of the present invention.

In the present invention, the section I represents the alarms G1~G3 of the normal states, and the sampling analysis value of the offline supports a reliability of the test result value. The offline analysis value of in the section II represents that the performance of a hydraulic oil is decreased as a consumption of an additive of an oil and a particle counter value are increased, and a particle of a metal wear such as Fe, Cu, etc. is increased. The test value of the present invention is G3 class and y1 which represents a pollution degree increase and needs a filter check. In the section III, the pollution degree of the oil and the wear degree of the metal are significantly increased. The exchanging time of the oil may be judged due to a loss of function of the oil. In particular, in the embodiment of the present invention, an alarm is generated by means of a lamp alarm or a sound alarm in the display unit based on the result value of the section III, so that it is possible to inform an oil pollution state and an oil exchange R1 to an operator.

FIG. 9 is a view illustrating an example that an emergency stop is generated when the sensor unit of the present invention detects an abnormal state by means of an upper graph and a lower graph. In the section III of FIG. 8, when the oil pollution degree is gradually increased, and the pollution degree value is high for a certain period, the oil exchange R1 is informed. As shown in FIG. 9, in the case that the sensor value of the oil pollution degree from the sensor unit is judged to be the normal classes G1~G3, and a certain abnormal state occurs in the hydraulic system due to a generation of a wear particle in a major component of the heavy equipment, the oil pollution degree is gradually increased like in the section A for a short time and then returns to the normal state. In the present invention, it is judged to be an abnormal state, and displays the emergency stop R2 for thereby informing the above state to the operator.

The heavy equipment having an oil pollution degree diagnosis function according to the present invention is capable of measuring an oil pollution degree in real time in a state that the heavy equipment is driven. In the case that it is judged to be a pollution, the pollution state is informed to the operator, so that it is possible to implement a safe operation of the heavy equipment. In addition, it is possible to implement an easier oil pollution degree measurement in such a manner that the sensor unit capable of measuring a variation of intensity of light which transmitted an oil and reflected, is fabricated in a module type. When a certain problem occurs therein, it is possible to exchange the same at a low cost.

In addition, in the oil pollution degree measuring system on the network and an operation method of the same according to the present invention, a sensor value concerning a state of an oil pollution from the sensor unit attached in a heavy equipment is measured, and a result value is computed from the sensor value by a diagnosis program, and the result value is stored in the oil pollution diagnosis server by the heavy equipment ID for thereby enhancing a durability and life span of the heavy equipment. In addition, it is possible to enhance a work efficiency in a work site and it is possible to prevent a danger accident due to a malfunction of the heavy equipment.

As described above, in the present invention, a heavy equipment having an oil pollution degree diagnosis function, an oil pollution degree measuring system on a network using the heavy equipment and an operation method of the same are implemented.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. In a heavy equipment having a hydraulic circuit comprising a hydraulic pump, a hydraulic motor, a major adjusting valve, a pipe, a hose, a hydraulic tank and an oil cooler, the improvement of an oil pollution degree diagnosis function, comprising:
    a sensor unit for oil to flow into an interior of the same from the hydraulic circuit and to measure an oil pollution state sensor value;
    a control unit to diagnose a normal/abnormal result value of the hydraulic circuit by an oil pollution state diagnosis program formed of a certain algorithm with respect to the sensor value;
    a communication unit which transfers the sensor and result values to the outside and receives a return value of a result of process from the outside;
    a storing unit which stores at least the result and return values; and
    a display unit which informs an oil pollution state to an operator based on the sensor value, result value and return value;
    whereby an oil pollution degree of the heavy equipment is measured by controlling the sensor unit, communication unit, storing unit and display unit by the control unit and is informed to the operator.

2. The improvement in the heavy equipment of claim 1, wherein said sensor unit includes:
    a sensor block which forms an outer construction of the same;
    an oil extracting apparatus which is installed in the hydraulic circuit in such a manner that an oil is flown thereinto, for thereby extracting an oil;
    a light emitting apparatus which is provided in a rear end of the oil extracting apparatus and generates a sensor light which transmits in the extracted oil;
    a reflection mirror which is installed in a front end of the oil extracting apparatus and reflects a sensor light which is transmitted in the extracted oil;
    a light receiving apparatus which is provided in a rear end of the oil extracting apparatus and measures an intensity of the reflection light which is transmitted in the extracted oil by the reflection mirror; and
    an optical sensor unit which inputs the light from the light emitting apparatus into the extracted oil as a parallel light and includes an optical transfer apparatus which transfers the reflection light which was reflected by the reflection minor and is transmitted in the monitored oil to the light receiving apparatus.

3. An oil pollution degree measuring system of a heavy equipment on a network as a system for remotely measuring and diagnosing an oil pollution degree between the heavy equipment and an oil pollution diagnosis server on a network, comprising:
    a hydraulic heavy equipment which includes a sensor unit which is installed in a hydraulic circuit of the heavy equipment in such a manner that an oil is flown into the interior of the same and extracts an oil flowing in the hydraulic circuit and measures an oil pollution state sensor value; a control unit which is adapted to diagnose a normal/abnormal state of a heavy equipment hydraulic system, filter check/exchange, oil exchange, emergency stop, etc. by an oil pollution state diagnosis program formed of a certain algorithm with respect to the sensor value detected through the sensor unit; a communication unit which receives a sensor value and a result value from the sensor unit and the control unit, respectively and transfers to the outside and receives a return value of a result of process from the outside; a storing unit which stores a sensor value of the sensor unit, a result value of the control unit, a return value of the communication unit, and other related data; and a display unit which informs an oil pollution state to an operator based on the sensor value, result value and return value; and
    an oil pollution diagnosis server which includes a server communication unit which receives an inherent heavy equipment ID, the sensor value and a receiving data including a result value from the communication units of a plurality of heavy equipments and transmits a return value corresponding to a result of a process to the communication unit of the heavy equipment corresponding to the heavy equipment ID; a storing unit which stores an engine driving time, measuring number, the sensor value and a receiving data including the result value based on the heavy equipment ID received from the server communication unit; and a server control unit which controls the server communication unit and the storing unit for processing the receiving data, whereby the heavy equipment measures an oil pollution state in a sensor value and determines a result value and transmits to the oil pollution diagnosis server, and the oil pollution diagnosis server receives a data from a plurality of the heavy equipments and stores the same and transmits a result return value to a corresponding heavy equipment.

4. An oil pollution degree measuring method of a heavy equipment on a network as a method for remotely measuring and diagnosing an oil pollution degree between the heavy equipment and an oil pollution diagnosis server on a network, comprising the steps of:

a step (1) in which an oil pollution state sensor value is measured by transmitting a sensor light in a sensor unit of a hydraulic circuit provide in a certain portion of the heavy equipment;

a step (2) in which a sensor value determines an oil pollution state result value by judging a normal/abnormal state of a heavy equipment hydraulic system, a filter check/exchange, oil exchange, emergency stop, by an oil pollution state diagnosis program in a control unit of the heavy equipment;

a step (3) in which a server communication unit of an oil pollution diagnosis server receives a sensor value and a result value from a communication unit of the heavy equipment;

a step (4) in which an engine driving time, a measuring number, and a data of the sensor value and result value based on a heavy equipment ID are stored in the storing unit in accordance with a control of the server control unit of the oil pollution diagnosis server;

a step (5) in which the server communication unit transfers a result of a process processed by the server control unit to a communication unit of the heavy equipment as a return value;

a step (6) in which a control unit of the heavy equipment displays an oil pollution state on a display unit based on the sensor value, result value and return value, whereby the heavy equipment measures an oil pollution state as a sensor value and determines a result value and transmits to the oil pollution diagnosis server, and the oil pollution diagnosis server receives a data from a plurality of heavy equipments and stores the same and transfers a result return value to an individual heavy equipment.

5. An oil pollution degree measuring system of a heavy equipment on a network as a system for remotely measuring and diagnosing an oil pollution degree between the heavy equipment and an oil pollution server on a network, comprising:

a hydraulic heavy equipment which includes a sensor unit which is installed in such a manner that an oil is flown into the interior of the same in a hydraulic circuit of the heavy equipment and is adapted to extract an oil flowing in the hydraulic circuit and to measure an oil pollution state sensor value; a communication unit which transfers a sensor value of the sensor unit to the server and receives a process result value concerning an oil pollution state from the server; a storing unit for storing a sensor value of the sensor unit, a result value of the communication unit and other related data; a display unit for informing an oil pollution state to an operator based on the sensor value and result value; and a control unit for controlling the sensor unit, communication unit, storing unit and display unit; and an oil pollution diagnosing server which includes a server communication unit which receives an inherent heavy equipment ID and a receiving data including the sensor data from a communication unit of a plurality of heavy equipments and transfers a result value corresponding to a process result to the communication unit of the heavy equipment corresponding to the heavy equipment ID; a server control unit which diagnoses a normal/abnormal state, filter check/exchange, oil exchange, emergency stop, of a hydraulic system of the heavy equipment by an oil pollution state diagnosis program formed of a certain algorithm with respect to a sensor value that the server communication received and determines an oil pollution state result value and transfers the result value to the server communication unit; and a storing unit which stores an engine driving time, measuring number, a receiving data including the sensor value and a result value data of the server control unit based on the heavy equipment ID received through the server communication unit;

whereby the heavy equipment measures an oil pollution state as a sensor value and transfers to the oil pollution diagnosis server, and the oil pollution diagnosis server receives a data from a plurality of the heavy equipments and determines an oil pollution state result value and transfers the result value to a corresponding heavy equipment.

6. An oil pollution degree measuring method of a heavy equipment on a network as a method for remotely measuring and diagnosing an oil pollution degree between the heavy equipment and an oil pollution diagnosis server on a network, comprising the steps of:

a step (1) in which an oil pollution state sensor value is measured by transmitting a sensor light in a sensor unit of a hydraulic circuit provide in a certain portion of the heavy equipment;

a step (2) in which a server communication unit of the oil pollution diagnosis server receives a sensor value from a communication unit of the heavy equipment;

a step (3) in which the sensor value is adapted to judge a normal/abnormal state of a heavy equipment hydraulic system, a filter check/exchange, an oil exchange, an emergency stop, by a certain oil pollution stare diagnosis program in the server control unit of the oil pollution diagnosis server, for thereby determining an oil pollution state result value;

a step (4) in which an engine driving time, measuring number, sensor value and result value data based on the heavy equipment ID are stored in the storing unit based on a control of the server control unit of the oil pollution diagnosis server;

a step (5) in which the server communication unit transfers a result processed by the server control unit to the communication unit of the heavy equipment as a result value; and a step (6) in which the control unit of the heavy equipment displays an oil pollution state on the display unit based on the sensor value and the result value, whereby the heavy equipment measures an oil pollution state as a sensor value and transfers to the oil pollution diagnosis server, and the oil pollution diagnosis server receives a data from a plurality of the heavy equipments and determines an oil pollution state result value and transfers the result value to a corresponding heavy equipment.

* * * * *